United States Patent
Fukuma et al.

(10) Patent No.: US 10,852,772 B2
(45) Date of Patent: Dec. 1, 2020

(54) INFORMATION PROCESSING APPARATUS AND INFORMATION PROCESSING METHOD

(71) Applicant: SONY CORPORATION, Tokyo (JP)

(72) Inventors: Yohei Fukuma, Chiba (JP); Toru Amano, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/086,411

(22) PCT Filed: Feb. 14, 2017

(86) PCT No.: PCT/JP2017/005235
§ 371 (c)(1),
(2) Date: Sep. 19, 2018

(87) PCT Pub. No.: WO2017/169202
PCT Pub. Date: Oct. 5, 2017

(65) Prior Publication Data
US 2019/0101959 A1    Apr. 4, 2019

(30) Foreign Application Priority Data

Mar. 28, 2016 (JP) ................................. 2016-063043

(51) Int. Cl.
*G06F 1/16* (2006.01)
*G06F 3/01* (2006.01)
(Continued)

(52) U.S. Cl.
CPC .............. *G06F 1/1675* (2013.01); *A61B 5/00* (2013.01); *A61B 5/0408* (2013.01);
(Continued)

(58) Field of Classification Search
CPC ....... G06F 1/163; G06F 1/1656; G06F 1/1684
(Continued)

(56) References Cited

U.S. PATENT DOCUMENTS 5,526,208 A  *  6/1996  Hatch ................... G11B 5/4846
                                                         360/294.1
5,774,096 A        6/1998  Usuki et al.
(Continued)

FOREIGN PATENT DOCUMENTS

EP        0679919 A2    11/1995
JP        08-005953 A    1/1996
(Continued)

OTHER PUBLICATIONS

International Search Report and Written Opinion of PCT Application No. PCT/JP2017/005235, dated May 9, 2017, 11 pages of English Translation and 10 pages of ISRWO.

*Primary Examiner* — Adrian S Wilson
(74) *Attorney, Agent, or Firm* — Chip Law Group

(57) ABSTRACT

An information processing apparatus according to an embodiment of the present technology includes a determination unit and an output unit. The determination unit determines, on a basis of information related to a usage state of a wearable device, a holding state of the wearable device with respect to an attachment target. The output unit generates and outputs control information for achieving the determined holding state.

11 Claims, 6 Drawing Sheets

(51) Int. Cl.
  *A61B 5/00* (2006.01)
  *A61B 5/0408* (2006.01)
  *A61B 5/11* (2006.01)
  *A61B 5/0478* (2006.01)
  *G02B 27/01* (2006.01)

(52) U.S. Cl.
  CPC .............. *A61B 5/0478* (2013.01); *A61B 5/11* (2013.01); *A61B 5/6801* (2013.01); *G02B 27/0176* (2013.01); *G06F 1/163* (2013.01); *G06F 3/016* (2013.01)

(58) Field of Classification Search
  USPC .................... 349/58–60; 361/679.55, 679.56
  See application file for complete search history.

(56) References Cited

U.S. PATENT DOCUMENTS

| | | | | |
|---|---|---|---|---|
| 6,833,656 B2* | 12/2004 | Hooley | ................ | H04R 17/00 310/328 |
| 7,252,313 B2* | 8/2007 | Browne | ................ | B29C 33/308 293/128 |
| 8,568,189 B2* | 10/2013 | Garbos | ................ | A63H 3/28 446/175 |
| 9,020,571 B2* | 4/2015 | Chi | ................ | H04B 1/38 455/575.1 |
| 9,116,546 B2* | 8/2015 | Birnbaum | ................ | G08B 6/00 |
| 9,510,470 B2* | 11/2016 | Huitema | ................ | G06F 1/1652 |
| 9,560,751 B2* | 1/2017 | Huitema | ................ | H05K 1/028 |
| 9,632,539 B2* | 4/2017 | Baldwin | ................ | G06F 1/1626 |
| 9,848,494 B2* | 12/2017 | Huitema | ................ | G06F 1/163 |
| D819,020 S * | 5/2018 | Choi | ................ | D14/341 |
| 10,206,623 B2* | 2/2019 | Harrison-Noonan | ................ | A61B 5/6843 |
| 10,285,645 B2* | 5/2019 | Bushnell | ................ | A61B 5/6843 |
| 10,289,163 B2* | 5/2019 | Huitema | ................ | G06F 1/163 |
| 10,394,192 B2* | 8/2019 | Ji | | |
| 2001/0043514 A1* | 11/2001 | Kita | ................ | A44C 5/0015 368/281 |
| 2003/0181116 A1* | 9/2003 | Van Heerden | ................ | G06F 3/016 442/182 |
| 2004/0239624 A1* | 12/2004 | Ramian | ................ | G06F 3/016 345/156 |
| 2004/0261411 A1* | 12/2004 | MacGregor | ................ | F03G 7/065 60/527 |
| 2006/0209218 A1* | 9/2006 | Lee | ................ | G04G 9/00 349/1 |
| 2007/0132551 A1* | 6/2007 | Mozer | ................ | E05B 47/0009 340/5.52 |
| 2008/0024963 A1* | 1/2008 | Weksler | ................ | G06F 1/1616 361/679.01 |
| 2009/0250267 A1* | 10/2009 | Heubel | ................ | G06F 3/016 178/18.03 |
| 2010/0253525 A1* | 10/2010 | Engel | ................ | G08B 6/00 340/573.1 |
| 2010/0283731 A1* | 11/2010 | Grant | ................ | G06F 3/016 345/158 |
| 2011/0102162 A1* | 5/2011 | Gregorio | ................ | G06F 3/016 340/407.2 |
| 2011/0121953 A1* | 5/2011 | Grant | ................ | A63F 13/245 340/407.1 |
| 2011/0188189 A1* | 8/2011 | Park | ................ | G05B 11/01 361/679.05 |
| 2011/0234502 A1* | 9/2011 | Yun | ................ | G06F 3/016 345/173 |
| 2012/0017702 A1* | 1/2012 | Kawabe | ................ | G06F 3/0414 73/862.381 |
| 2014/0180582 A1* | 6/2014 | Pontarelli | ................ | G01C 21/20 701/494 |
| 2014/0275852 A1* | 9/2014 | Hong | ................ | A61B 5/02427 600/301 |
| 2014/0307369 A1* | 10/2014 | Lee | ................ | H04M 1/0216 361/679.01 |
| 2015/0091711 A1* | 4/2015 | Kosonen | ................ | G08B 6/00 340/407.1 |
| 2015/0185764 A1* | 7/2015 | Magi | ................ | G06F 1/163 361/679.03 |
| 2015/0185944 A1* | 7/2015 | Magi | ................ | G06F 1/1652 345/174 |
| 2015/0186705 A1* | 7/2015 | Magi | ................ | G06K 9/0002 382/125 |
| 2015/0265214 A1* | 9/2015 | De Kok | ................ | A61B 5/6843 600/301 |
| 2015/0378391 A1* | 12/2015 | Huitema | ................ | H05K 5/0017 361/679.03 |
| 2016/0071408 A1* | 3/2016 | Jiao | ................ | A61B 5/6802 600/300 |
| 2016/0077553 A1* | 3/2016 | Hyun | ................ | G06F 3/0412 345/690 |
| 2016/0187935 A1* | 6/2016 | Tazbaz | ................ | G06F 1/1616 361/679.03 |
| 2016/0195928 A1* | 7/2016 | Wagner | ................ | G06F 3/016 345/156 |
| 2016/0255944 A1* | 9/2016 | Baranski | ................ | A44C 5/0069 |
| 2016/0287103 A1* | 10/2016 | Saponas | ................ | A61B 5/02233 |

FOREIGN PATENT DOCUMENTS

| | | |
|---|---|---|
| JP | 2006-288663 A | 10/2006 |
| JP | 2007-330638 A | 12/2007 |

* cited by examiner

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2017/005235 filed on Feb. 14, 2017, which claims priority benefit of Japanese Patent Application No. JP 2016-063043 filed in the Japan Patent Office on Mar. 28, 2016. Each of the above-referenced applications is hereby incorporated herein by reference in its entirety.

TECHNICAL FIELD

The present technology relates to an information processing apparatus, an information processing method, and a program that are applicable to a wearable device.

BACKGROUND ART

From the past, various wearable devices of a glasses type, a wristwatch type, and the like have been used. For example, Patent Literature 1 describes a glasses-type head-mounted display (HMD) that can be worn on a head of a user. In the HMD described in Patent Literature 1, a band member that couples two display units for a right eye and a left eye is formed to be curved so that it can be arranged around the head of the user. Further, a wiring member that electrically connects the two display units is arranged inside the band member. Accordingly, it becomes possible to obtain a proper fit while reducing a feeling of fatigue when wearing the device (paragraphs [0034] and [0038], FIGS. 1A, 1B, and 2, etc. of Patent Literature 1).

CITATION LIST

Patent Literature

Patent Literature 1: Japanese Patent Application Laid-open No. 2015-126397

DISCLOSURE OF INVENTION

Technical Problem

It is considered that wearable devices will prevail from now on, and a technology that enables wearable devices to be worn with a proper fit is required.

In view of the circumstances as described above, an object of the present technology is to provide an information processing apparatus, an information processing method, and a program that enable a wearable device to be worn with a proper fit.

Solution to Problem

To attain the object described above, an information processing apparatus according to an embodiment of the present technology includes a determination unit and an output unit.

The determination unit determines, on a basis of information related to a usage state of a wearable device, a holding state of the wearable device with respect to an attachment target.

The output unit generates and outputs control information for achieving the determined holding state.

In this information processing apparatus, the holding state with respect to the attachment target is determined on the basis of the information related to the usage state of the wearable device. Therefore, it becomes possible to achieve a fit corresponding to the usage state and wear the wearable device with a proper fit.

The determination unit may determine the usage state of the wearable device and determine the holding state corresponding to the determined usage state.

Accordingly, it becomes possible to determine the holding state corresponding to the usage state.

The holding state may include a holding force and a holding position with respect to the attachment target.

Accordingly, it becomes possible to control the holding force and the holding position in accordance with the usage state and achieve a proper fit.

The information related to the usage state may include state information of a user who uses the wearable device.

Accordingly, it becomes possible to achieve a fit corresponding to the state of the user.

The state information of the user may include motion information, biological information, and positional information.

Accordingly, it becomes possible to control the holding state with high accuracy.

The motion information may include a result of a behavior analysis of the user.

By the behavior analysis, it becomes possible to acquire the motion information with high accuracy.

The determination unit may determine a first motion state of the user on a basis of the motion information and a second motion state in which a motion amount is larger than that of the first motion state, and determine, in accordance with the second motion state, a second holding state in which the holding force is larger than that of a first holding state determined in accordance with the first motion state.

Accordingly, it becomes possible to achieve a proper fit corresponding to the motion state.

The determination unit may restrict the holding force on a basis of the biological information.

Accordingly, it becomes possible to achieve a proper fit corresponding to a physical condition.

The determination unit may restrict the holding force in a case where a predetermined user state is determined on a basis of the biological information.

Accordingly, it becomes possible to exert a holding force corresponding to the physical condition.

The determination unit may restrict the holding force by setting an upper limit value of the holding force.

Accordingly, it becomes possible to easily restrict the holding force and exert a holding force corresponding to the physical condition.

The information related to the usage state may include state information of the wearable device.

Accordingly, it becomes possible to achieve a holding state corresponding to an apparatus state of the wearable device.

The state information of the wearable device may include information related to a function of the wearable device.

Accordingly, it becomes possible to achieve a holding state corresponding to the function to be executed.

The information related to the usage state may include information of a usage environment of the wearable device.

Accordingly, it becomes possible to achieve a holding state corresponding to the usage environment.

The information related to the usage state may include information of the attachment target.

Accordingly, it becomes possible to achieve the holding state corresponding to a type of the attachment target and a part to be attached.

The determination unit may set a plurality of candidate holding states as candidates of the holding state, and select the holding state from the plurality of candidate holding states.

Accordingly, it becomes possible to accurately determine an appropriate holding state corresponding to the usage state.

The determination unit may set a basic holding state and determine the holding state by changing the basic holding state on a basis of the information related to the usage state of the wearable device.

Accordingly, it becomes possible to determine the holding state corresponding to the change of the usage state.

The determination unit may be capable of determining a state where a plurality of mutually-different holding states change continuously, as the holding state.

Accordingly, a proper fit can be achieved.

An information processing method according to an embodiment of the present technology is an information processing method executed by a computer system, the method including determining, on a basis of information related to a usage state of a wearable device, a holding state of the wearable device with respect to an attachment target.

Control information for achieving the determined holding state is generated and output.

A program according to an embodiment of the present technology causes a computer system to execute the following steps.

The step of determining, on a basis of information related to a usage state of a wearable device, a holding state of the wearable device with respect to an attachment target.

The step of generating and outputting control information for achieving the determined holding state.

Advantageous Effects of Invention

As described above, according to the present technology, it becomes possible to wear the wearable device with a proper fit. It should be noted that the effects described herein are not necessarily limited, and any effect described in the present disclosure may be obtained.

MODES FOR CARRYING OUT THE INVENTION

Hereinafter, embodiments of the present technology will be described with reference to the drawings.

[Wearable Apparatus]

Figure 1A:
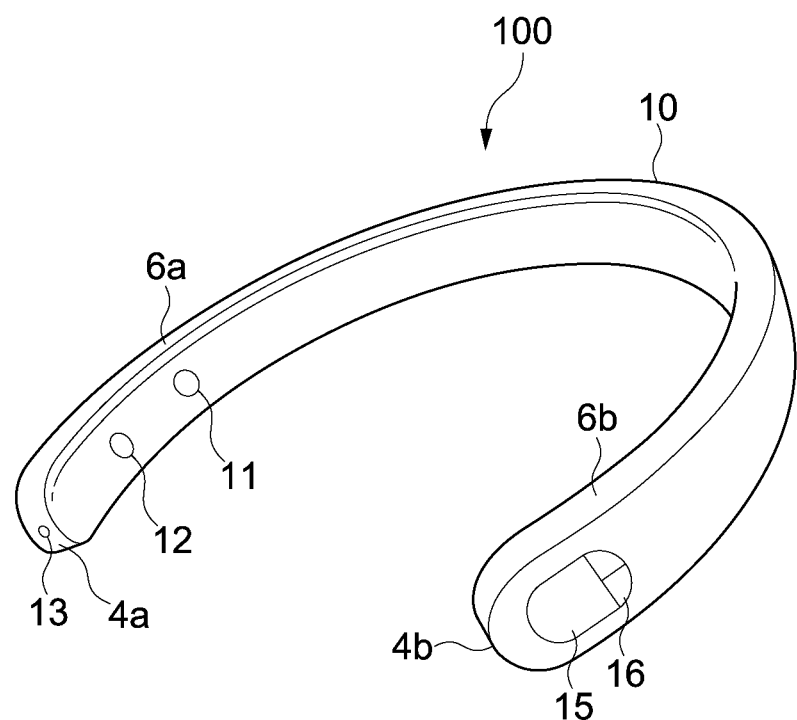
FIGS. 1A and 1B Schematic diagrams showing a configuration example of a wearable apparatus according to an embodiment of the present technology.
Figure 1B:
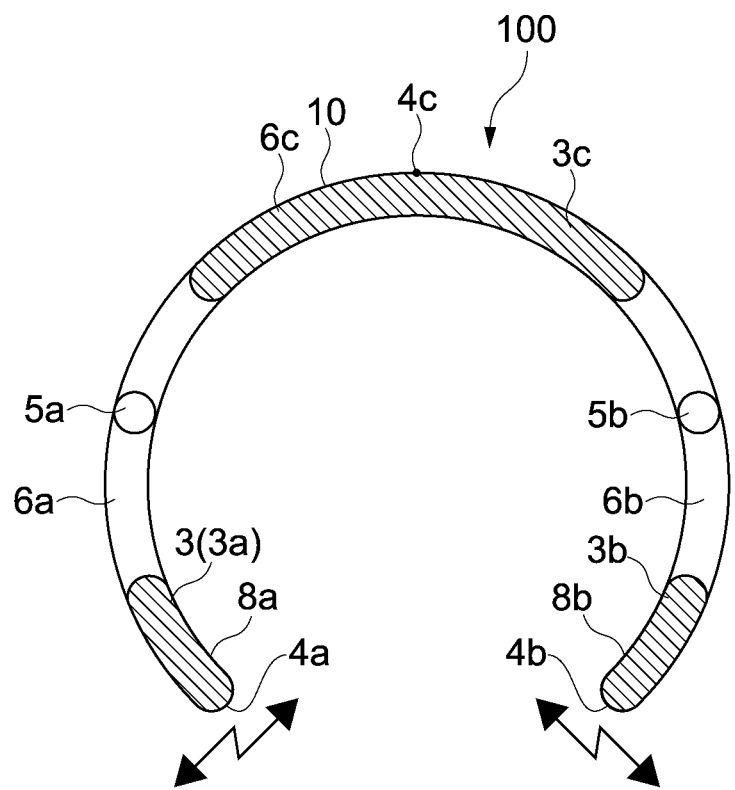
Figure 2:
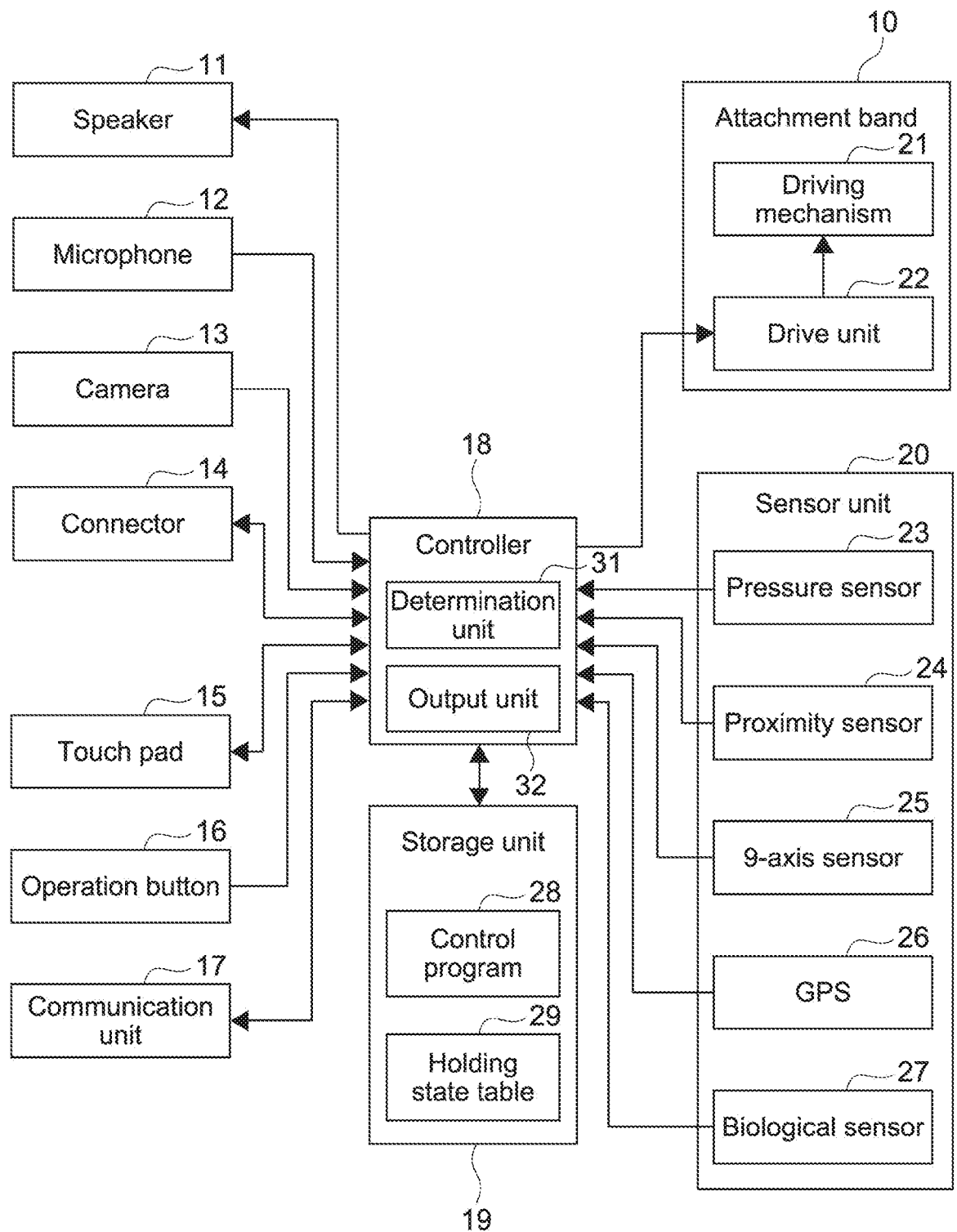
FIG. 2 A block diagram showing a functional configuration example of the wearable apparatus shown in FIGS. 1A and 1B.

FIGS. 1A and 1B are schematic diagrams showing a configuration example of a wearable apparatus according to an embodiment of the present technology. FIG. 1A is a perspective view showing an outer appearance, and FIG. 1B is a schematic diagram for explaining an internal configuration. FIG. 2 is a block diagram showing a functional configuration example of the wearable apparatus. A wearable apparatus 100 is a neckband-type wearable device and is worn on a neck of a user to be used.

The wearable apparatus 100 includes an attachment band 10, speakers 11, microphones 12, a camera 13, a connector 14, a touch pad 15, an operation button 16, and a communication unit 17. The wearable apparatus 100 also includes a controller 18, a storage unit 19, a sensor unit 20, a driving mechanism 21, and a drive unit 22. The controller 18, the storage unit 19, and the sensor unit 20 are provided inside a system block 3 in the attachment band 10 shown in FIG. 1B.

The attachment band 10 has flexibility and is made of, for example, plastic, rubber, or the like. As shown in FIG. 1A, the attachment band 10 has a substantially U shape and is worn on a neck such that end portions 4a and 4b thereof are positioned on a front side. Hereinafter, the end portions 4a and 4b side may be referred to as front side, and the opposite side may be referred to as rear side.

As shown in FIG. 1B, hinges 5a and 5b are respectively provided substantially at center positions between the end portions 4a and 4b and a rearmost end 4c in the attachment band 10. Left- and right-hand front arms 6a and 6b are rotatable with respect to a rear base portion 6c via the hinges 5a and 5b.

The speakers 11 are respectively provided at predetermined positions of the left- and right-hand front arms 6a and 6b, from the end portions 4a and 4b toward the rear side. For example, telephone-call audio, an audio guidance, an alarm sound, music content, and the like are output from the speakers 11. The microphones 12 are respectively provided in the vicinity of the end portions 4a and 4b of the left- and right-hand front arms 6a and 6b. Instruction inputs by telephone calls and voices, and the like can be made via the microphones 12.

The camera 13 is provided at the end portion 4a of the right-hand front arm 6a. For example, a digital camera including an image sensor such as a CMOS (Complementary Metal-Oxide Semiconductor) sensor and a CCD (Charge Coupled Device) sensor is used.

The connector 14 is a terminal for connecting with other devices. Terminals for USB (Universal Serial Bus), HDMI (registered trademark) (High-Definition Multimedia Interface), and the like are provided, for example. Further, during charging, a charge terminal of a charge dog (cradle) and the connector 14 are connected so as to perform charging.

The touch pad 15 and the operation button 16 are provided on an outer side of the left-hand front arm 6b. With the touch pad 15 and the operation button 16, it becomes possible to execute an operation of turning on/off power supply and operations related to various functions of the wearable apparatus 100, such as a photographing function of the camera 13 and a network communication function.

The communication unit 17 is a module for executing network communication, short-distance wireless communication, and the like with other devices. For example, a wireless LAN module such as WiFi and a communication module such as Bluetooth (registered trademark) are provided.

The sensor unit 20 includes pressure sensors 23, a proximity sensor 24, a 9-axis sensor 25, a GPS 26, and a biological sensor 27. The pressure sensors 23 are respectively provided in left- and right-hand system blocks 3a and 3b shown in FIG. 1B. The pressure sensors 23 are capable of measuring pressures applied to left- and right-hand side portions of the neck. In this embodiment, a holding force with which the attachment band 10 holds the neck as an attachment target, is measured on the basis of a detection result of the pressure sensors 23.

The holding force is a force with which the attachment band 10 holds the attachment target, and a state where the attachment band 10 is securely attached to the attachment target without deviation is a state where the holding force is high. On the other hand, a state where the attachment band 10 moves up and down or rotates is a state where the holding force is low. The holding force is typically controlled by controlling the pressures to be applied to the attachment target. Meanwhile, the holding force may also be controlled by controlling a size of a contact area regarding the attachment target or controlling an adhesive force or the like. In other words, the method of controlling the holding force is not limited, and various methods may be used.

The proximity sensor 24 is provided on an inner circumferential side of the attachment band 10, and a detection result thereof is used for determining whether or not the wearable apparatus 100 is worn. The 9-axis sensor 25 includes a triaxial acceleration sensor, a triaxial gyro sensor, and a triaxial compass sensor. The 9-axis sensor 25 is capable of detecting accelerations, angular velocities, and orientations of the wearable apparatus 100 along three axes. The GPS 26 acquires information on a current position of the wearable apparatus 100. These sensors are provided in a system block 3c on a rear side where there is little deviation due to a shake and the like. As a result, detection accuracy can be improved.

The biological sensor 27 acquires biological information of the user. For example, as the biological sensor 27, a temperature sensor capable of measuring a body temperature, a heartbeat sensor capable of measuring a heart rate, a perspiration sensor capable of measuring a perspiration amount, and the like are provided. These sensors are provided at predetermined positions of the wearable apparatus 100 such that the sensor units come into contact with predetermined positions of the body. For example, the heartbeat sensor is provided at a position where it can be brought into contact with a blood vessel of the neck. The positions where the respective sensors are provided are stored in advance.

The types of sensors to be provided as the sensor unit 20 are not limited, and an arbitrary sensor may be provided. For example, a temperature sensor, a humidity sensor, and the like that are capable of measuring a temperature, humidity, and the like of an environment where the wearable apparatus 100 is used may be provided.

The storage unit 19 is a nonvolatile storage device, and an HDD (Hard Disk Drive) or the like is used, for example. The storage unit 19 stores a control program 28 for controlling an overall operation of the wearable apparatus 100. The storage unit 19 also stores a holding state table 29. The holding state table 29 is a table in which a usage state of the wearable apparatus 100 and a holding state of the attachment band 10 are associated with each other. A method of installing the control program 28 and the holding state table 29 in the wearable apparatus 100 is not limited.

The driving mechanism 21 is a mechanism for changing the holding state of the attachment band 10 with respect to the user. In this embodiment, the driving mechanism 21 includes the left- and right-hand hinges 5a and 5b shown in FIG. 1B and an actuator mechanism (not shown) for rotating the left- and right-hand front arms 6a and 6b. As the actuator mechanism, for example, an arbitrary configuration that uses a motor, a piezoelectric device, a wire, a solenoid, a shape-memory alloy (SMA), and the like may be used.

The drive unit 22 controls an operation of the driving mechanism 21 on the basis of control information output from the controller 18. In this embodiment, the left- and right-hand front arms 6a and 6b are rotated to control the holding force. The holding force becomes high when the front arms 6a and 6b are tightened so as to approach each other. The holding force becomes low when the front arms 6a and 6b are released to be set apart from each other.

Here, a position of a portion of the wearable apparatus 100 that exerts the holding force by coming into contact with the attachment target is set as a holding position of the wearable apparatus 100. In this embodiment, front-side portions of the left- and right-hand front arms 6a and 6b become the holding positions 8a and 8b. Of course, the base portion 6c on the rear side also holds the neck.

The controller 18 controls operations of the respective block of the wearable apparatus 100. The controller 18 includes a hardware configuration requisite for a computer, such as a CPU and a memory (RAM, ROM). Various types of processing are executed by the CPU loading the control program 28 stored in the storage unit 19 into the RAM and executing it.

As the controller 18, for example, PLD (Programmable Logic Device) such as FPGA (Field Programmable Gate Array), or other devices such as ASIC (Application Specific Integrated Circuit) may be used.

In this embodiment, the CPU of the controller 18 executes a program according to this embodiment, to thus realize a determination unit 31 and an output unit 32 as functional blocks. The determination unit 31 determines the holding state of the attachment band 10 with respect to the attachment target on the basis of information related to the usage state of the wearable apparatus 100. The output unit 32 generates and outputs control information for achieving the determined holding state.

Therefore, in this embodiment, an information processing method according to this embodiment is executed by the controller 18. It should be noted that dedicated hardware may be used as appropriate to realize the determination unit 31 and the output unit 32.

The information on the usage state of the wearable apparatus 100 can be acquired by the controller 18 on the basis of the detection result from the sensor unit 20, for example. Here, the information related to the usage state includes various types of information related to a state where the wearable apparatus 100 is used. For example, information related to a state of the user using the wearable apparatus 100, information related to a state of the wearable apparatus 100 to be used, information related to a usage environment where the wearable apparatus 100 is used, and the like are included.

Motion information related to a motion of the user is acquired as user state information. For example, information of walking, traveling, traveling by train, driving, and the like is acquired. Information on a type of sports being performed can also be acquired. In addition, information related to a posture as in sitting, standing, bending forward, facing sideways, facing upwards, and the like is acquired.

Further, information related to a current position of the user, more specifically, whether the user is currently indoor, outdoor, in midst of a meeting, or the like, can also be acquired. Furthermore, information on whether the user is asleep or awake, and biological information such as a body temperature, a pulse rate, and a perspiration amount are also acquired. These pieces of user state information can be acquired by an arbitrary behavior analysis technology such as a behavior analysis that uses parameters obtained by machine learning, and the like, for example.

As information of an apparatus state of the wearable apparatus 100, various types of information such as a function being executed, an operation mode, whether the apparatus is attached to the attachment target, an attachment position with respect to the user, a remaining battery amount, connection with the charge dock, and an apparatus temperature, are acquired. Various types of information such as a temperature, a humidity, a current position, weather, and date and time are acquired as the information on the usage environment. Sensors, devices, and the like for acquiring these pieces of information are provided in the wearable apparatus 100 as appropriate.

Further, the user state information, apparatus state information, and usage environment information may be acquired on the basis of communication with an apparatus mounted on an automobile or the like, information on a network, and the like.

The controller 18 determines the usage state of the wearable apparatus 100 on the basis of usage state information related to the acquired usage state. The usage state includes the user state, the apparatus state of the wearable apparatus 100, the usage environment, and the like.

[Control of Holding State]

Figure 3:
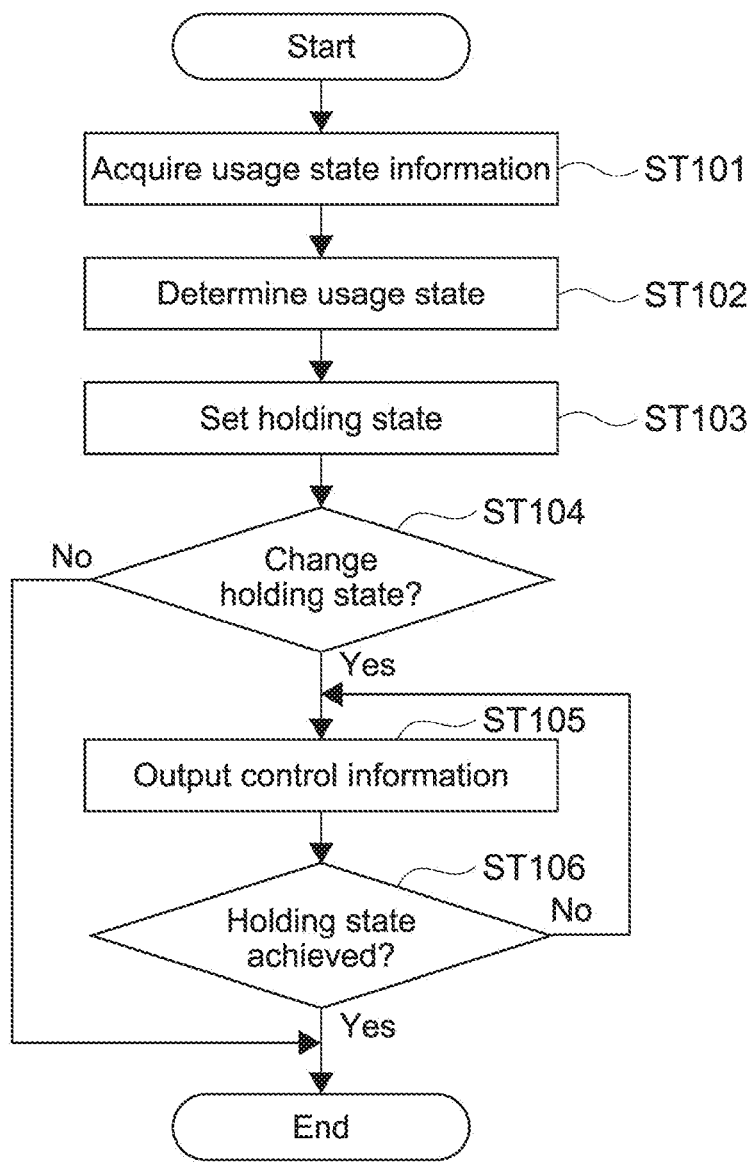
FIG. 3 A flowchart showing a control example of a holding state of an attachment band.

FIG. 3 is a flowchart showing a control example of the holding state of the attachment band 10. First, the usage state information related to the usage state is acquired (Step 101). The usage state is determined on the basis of the acquired usage state information (Step 102). For example, the user state information, apparatus information of the wearable apparatus 100, environment information of the usage environment, or the like described above are monitored, and a predetermined usage state is determined in a case where a predetermined condition is satisfied.

The holding state corresponding to the usage state is determined (Step 103). The holding state is stored in the holding state table 29 stored in the storage unit 19. By referencing the holding state table 29, the controller 18 determines the holding state corresponding to the usage state. Of course, the method is not limited to the method that uses table information, and the attachment state may be calculated as appropriate by a calculation or the like. An arbitrary holding state can be allocated as the holding state corresponding to the usage state, and a specific example will be given later.

In order to achieve the determined holding state, it is determined whether a current holding state needs to be changed (Step 104). The current holding state can be determined on the basis of the detection result from the sensor unit 20. In this embodiment, the current holding state is determined on the basis of the detection results from the pressure sensors 23 respectively provided in the left- and right-hand system blocks 3a and 3b.

In a case where it is determined that the holding state does not need to be changed (No in Step 104), the holding state is maintained. In a case where it is determined that the holding state needs to be changed (Yes in Step 104), control information for achieving the determined holding state is output to the drive unit 22 (Step 105). Accordingly, the driving mechanism 21 is operated, and at least one of the front arms 6a and 6b is rotated. As a result, the holding state, more specifically, the holding force and the holding position, are changed.

Whether the holding state is achieved is determined on the basis of the detection result from the sensor unit 20 (Step 106). In a case where it is not achieved (No), control information is generated and output as appropriate. Specifically, in this embodiment, information on the holding state is fed back to the controller 18 by the sensor unit 20 or the like. As a result, the holding state can be controlled with high accuracy. When the holding state is achieved (Yes in Step 106), the processing is ended.

An example of determining the usage state and the holding state corresponding thereto according to this embodiment will be described.

For example, examples of the holding state corresponding to the user state are shown below. It should be noted that the respective states of weak, medium, and strong regarding the holding force correspond to weak, medium, and strong regarding a pressing force of the front arms 6a and 6b against the neck. Further, a specific pressing force is not limited, and a magnitude of the holding force is controlled relatively.

User state: normal (still) . . . holding state: weak holding force

User state: walking . . . holding state: medium holding force

User state: traveling on vehicle . . . hold state: strong holding force

User state: riding on bicycle while standing . . . holding state: medium holding force User state: riding on bicycle while sitting on saddle . . . holding state: weak holding force User state: playing golf . . . holding state: medium holding force User state: playing tennis . . . holding state: strong holding force These examples are processing based on an idea that the holding force is to be increased in a case where there is a high possibility that the wearable apparatus 100 will be displaced due to an exercise and the like. For example, it is assumed that a first motion state and a second motion state having a larger motion amount than that of the first motion state can be respectively determined on the basis of motion information. Then, it is assumed that a first holding state is determined in accordance with the first motion state and a second holding state is determined in accordance with the second motion state. In this case, the holding force in the second holding state is typically set to be larger than that in the first holding state. For example, even in the same running state, the higher the speed, the larger the motion amount, so the holding force is set to become large.

It should be noted that the motion state where the motion amount is large is typified by a motion state that requires large energy consumption such as a high speed, a large amount of movement of arms, legs, and the like, and a higher jump. In addition, an arbitrary motion state that is generally determined to have a large motion amount is also included.

It should be noted that depending on the purpose of the user, it is of course possible to make determinations different from the examples described above. For example, in a case where it is considered that pressing on the neck hinders concentration during an exercise, a determination of slightly lowering the holding force as the exercise becomes intense may be taken. For example, in a case where an influence of a shake of the wearable apparatus 100 is small, or the like, the determination as follows is executed.

It is also possible to determine the usage state that changes each moment as appropriate and determine the holding state in real time. For example, in a case where a traveling speed of the user increases, motion information thereof is acquired in real time, and the holding state corresponding to the motion information is determined as appropriate. As a result, it becomes possible to raise the holding force in accordance with the increase of the traveling speed.

User state: tilting body . . . holding state: medium holding force

User state: sitting while bending . . . holding state: medium holding force

User state: sitting up straight . . . holding state: weak holding force

This is an example of determining the holding force corresponding to the posture of the user, and in a case of a posture in which the wearable apparatus 100 highly likely falls off, the holding force is raised. Alternatively, it is also possible to determine the bent state as a concentrated state, and control to slightly weaken the holding force so as not to disturb the concentration may be performed.

User state: sleeping . . . holding state: weak holding force

User state: small perspiration amount . . . holding state: medium holding force

User state: large perspiration amount . . . holding state: strong holding force

For example, in a case where the user is sleeping, the holding force is weakened so as not to wake the user up. Alternatively, the holding state may be set to be zero. The state where the holding force is zero is, for example, a state where the wearable apparatus 100 is merely placed on the neck. For example, it is also possible to set a distance between the front arms 6a and 6b as appropriate and register that state as a state where the holding force is zero.

The holding force may be restricted on the basis of the biological information acquired from the biological sensor 27. For example, the holding force is restricted in a case where a state where a physical condition is poor, a state where various symptoms may appear, a state where the user feels uncomfortable (collectively referred to as poor physical condition state), or the like is determined as a predetermined state of the user. For example, as a holding state corresponding to the poor physical condition state, a holding state where the holding force is low or the holding force becomes zero is determined. Alternatively, in a case where the poor physical condition state is determined, an upper limit value may be set for the holding force so that the holding force is determined within a range equal to or smaller than the upper limit value. It is also possible to restrict the holding force by setting the upper limit value in this way.

For example, in a case where the poor physical condition state is determined while the holding force is being raised in accordance with an increase of the motion amount, the holding force is restricted. Accordingly, it becomes possible to sufficiently reduce a load on the user and take appropriate measures for the poor physical condition state. Of course, if a low-load state where the load on the user is smallest is a state where the displacement of the wearable apparatus 100 is suppressed while exerting a certain amount of holding force, that holding state may be selected.

An example of the holding state corresponding to the apparatus state will be described.

Apparatus state: photographing mode ON . . . holding state: holding force of right-hand front arm 6a is strong Apparatus state: photographing mode OFF . . . holding state: weak holding force Apparatus state: stereotactic sound field ON . . . holding state: medium holding force Apparatus state: stereotactic sound field OFF . . . holding state: weak holding force Apparatus state: NC mode ON . . . holding state: medium holding force Apparatus state: NC mode OFF . . . holding state: weak holding force In a case where the photographing mode that uses the camera 13 is ON, the right-hand front arm 6a is tightened so that the camera 13 does not shake. As a result, the holding force of only the holding position 8a is controlled. In this way, it is also possible to control the holding force for each holding position. The stereotactic sound field ON is a mode for holding an orientation of sound to be output from the speakers 11, and the holding force is raised so that the positions of the speakers 11 are not deviated. For example, in a case where an audio guidance for a landscape or the like is output by an application for a guide of tourist spots, the stereotactic sound field is set to ON, and the holding force is raised. In a case of executing the NC mode (noise canceling mode), the holding force is raised so that the positions of the microphones 12 to which noises are input and the speakers 11 that output antiphase sound are not deviated. This achieves highly accurate NC.

Apparatus state: pulse measurement mode ON . . . holding state: holding force of portion including pulse sensor is strong In the case of acquiring biological information of the user such as a pulse, the holding force and the holding position are determined as appropriate for fixing the respective sensors at predetermined measurement positions. Accordingly, biological information can be accurately measured. The change of the holding state for the measurement may be executed in conjunction with a measurement time, for example, after an elapse of a predetermined time since getting up, after an elapse of a predetermined time since having a meal, and the like. This achieves an efficient and accurate measurement.

The holding force may be raised when the wearable apparatus 100 is connected to the charge dog. For example, the wearable apparatus 100 is mounted on a cradle having a predetermined shape. The controller 18 acquires cradle information as information of the attachment target. The holding state is controlled to exert a strong holding force in accordance with this information. Accordingly, the connection with the charge dog is strengthened, and charging is reliably performed. It is also possible to design an overall shape of the charge dog and the wearable apparatus 100 during charging in a small size. Further, by closing the front arms 6a and 6b, a predetermined shape of a character or the like may be formed by the charge dog and the wearable apparatus 100. It should be noted that the holding state may be changed in a case where the wearable apparatus 100 is simply connected to the charge dog.

Examples of the holding state corresponding to the usage environment will be given.

Usage environment: underwater . . . holding state: strong holding force

Usage environment: on land . . . holding state: weak holding force

Usage environment: strong wind . . . holding state: medium holding force

Usage environment: calm . . . holding state: weak holding force

Usage environment: cold . . . holding state: strong holding force

Usage environment: hot . . . holding state: weak holding force

For example, in a state where there is a high possibility that the wearable apparatus 100 will move like underwater, the holding force is set to be higher than that in the case of being used on land. Further, in a case where the wind is strong, the holding force is strengthened, and the wearable apparatus 100 is sufficiently fixed. In a case where it is cold with a low temperature, the wearable apparatus 100 is tightened, and the body is warmed by the heat of the wearable apparatus 100, for example. On the other hand, in a case where the temperature of the wearable apparatus 100 becomes high regardless of the temperature, the holding force is weakened or the holding force is set to be zero. Accordingly, high safety can be exerted.

As the usage state determined in Step 102, a case that a state where different usage states including the user state, the apparatus state, the usage environment, and the like described above are combined is determined, is also possible. Examples thereof include a state where the audio guidance is output while the user is walking and activating the camera, a state where the pulse measurement mode becomes ON while the temperature is high and the wind is strong, and the like.

The state where the plurality of usage states are combined can also be regarded as one usage state, and a holding state corresponding to that usage state is determined. Several examples of the method of determining the holding state in this case will be described. It should be noted that regarding the combination of the plurality of usage states, the plurality of usage states may occur at the same timing, or the plurality of usage states may overlap with time.

For example, it is assumed that a state where the first usage state, the second usage state, and the third usage state are combined is determined. Here, the holding states respectively corresponding to the first to third usage states are assumed to be the first holding state, the second holding state, and the third holding state.

For example, in Step 103, the first to third holding states are set as a plurality of candidate holding states as candidates for the holding state, and one holding state is selected from these holding states on the basis of a predetermined condition. For example, of the plurality of candidate holding states, the holding state having the highest holding force is selected. Alternatively, a predetermined priority is set as a parameter with respect to the usage states, and a candidate holding state corresponding to the usage state with a high priority is selected.

For example, it is assumed that the following usage states have been combined.

User state: normal (still) . . . holding state: weak holding force

Apparatus state: photographing mode ON . . . holding state: holding force of right-hand front arm 6a is strong Usage environment: calm . . . holding state: weak holding force In this case, the holding state that has the highest holding force and corresponds to the photographing mode ON is determined.

User state: riding bicycle while sitting on saddle . . . holding state: weak holding force Apparatus state: stereotactic sound field OFF . . . holding state: weak holding force Usage environment: cold . . . holding state: strong holding force In this case, the holding state in the case where the holding power is the strongest and the temperature is low is determined.

User state: normal (still) . . . holding state: weak holding force

Apparatus state: stereotactic sound field ON . . . holding state: medium holding force User state: blood pressure is higher than predetermined value . . . holding state: weak holding force For example, in a case where a blood pressure value of a level at which congestion may occur is measured, a holding state corresponding to that user state is selected, and the holding force is weakened. The state where a blood pressure value of a level at which congestion may occur is measured is a state included in the poor physical condition state described above. By setting a high priority to the poor physical condition state, it is possible to restrict the holding force as described above. As a result, it becomes possible to achieve a fit according to the physical condition of the user and the like and thus improve safety.

User state: normal (still) . . . holding state: weak holding force

Apparatus state: apparatus temperature is higher than predetermined value . . . holding state: holding force is zero Usage environment: cold . . . holding state: strong holding force For example, in a case where the apparatus temperature is equal to or higher than a temperature at which low temperature burn may occur due to contact for a long time, the holding state corresponding to that apparatus state is determined, and the holding force is controlled to become zero. In this case, a high priority is given to the apparatus information.

In a case where a plurality of usage states overlap one another over time, a holding state corresponding to that usage state is determined at a timing when a usage state with a high holding force or a usage state with a high priority occurs, for example.

Alternatively, on the basis of the first to third holding states, a fourth holding state corresponding to the usage state obtained by the combination may be newly determined. For example, it is assumed that the first to third usage states are combined in the stated order. In this case, the first holding state corresponding to the first usage state determined earliest is set as the basic holding state. On the basis of this basic holding state, the holding state is changed so as to become close to the second holding state and the third holding state. The holding state after the change becomes the fourth holding state.

For example, the holding force is set to medium since the user is walking (basic holding state), and then the camera is activated, so only the right-hand front arm 6a is made strong from the state where the holding force is medium. Then, in accordance with an output of the audio guidance, the left-hand front arm 6b is made strong, and the holding forces of the left- and right-hand front arms 6a and 6b are both made strong.

Further, since the temperature is extremely high, the holding force is set to zero (basic holding state), and in accordance with a measurement of the strong wind, the holding force is strengthened from zero to medium. After that, the pulse measurement mode is set, and the holding state is changed so that the pulse sensor comes into contact with the neck from the state where the holding force is medium. The change from the basic holding state may be executed as in these examples.

It is assumed that a holding state corresponding to a motion state having a large motion amount of is set as the basic holding state, and the poor physical condition state is determined after that. In this case, it is also possible to perform control such that the holding force is changed up to the upper limit value set in accordance with the poor physical condition state or the holding force is changed toward zero.

A state where a plurality of mutually-different holding states change continuously may be determined as the holding state corresponding to the usage state. For example, in a case where a strong holding force is wished to be exerted during traveling or the like, a plurality of holding states such as a weak holding force, a medium holding force, maintain a holding force for a predetermined time, and a strong holding force may be continuously changed in this order. A holding state including this change is determined in accordance with a predetermined usage state. As a result, it becomes possible to suppress an uncomfortable feeling or the like caused by a sudden change in the holding force. Further, fine setting of the holding state becomes possible.

Further, it is also possible to sequentially strengthen the respective holding forces at the plurality of holding positions in a case where a strong holding force is wished to be exerted. For example, a plurality of holding states such as a medium holding force of the right-hand front arm 6a, a medium holding force of the left-hand front arm 6b, a strong holding force of the right-hand front arm 6a, and a strong holding force of the left-hand front arm 6b may be executed continuously in this order. It is also possible to determine such a holding state stepwise. Furthermore, control in which different holding states are repetitively executed is also possible.

As described above, in the wearable apparatus 100 according to this embodiment, the holding state with respect to the attachment target is determined on the basis of the information related to the usage state of the wearable apparatus 100. Therefore, it becomes possible to achieve a fit corresponding to the usage state and wear the wearable device with a proper fit. Specifically, it becomes possible to highly accurately control the holding force and the holding position with high precision in accordance with the user state, the apparatus state of the wearable apparatus 100, the usage environment, and the like.

Other Embodiments

The present technology is not limited to the embodiment described above, and various other embodiments can be realized.

FIGS. 4A, 4B, 4C, 5A, 5B, and 5C are schematic diagrams showing another configuration example of the driving mechanism. In the driving mechanism shown in FIG. 4A, one hinge 5 is provided at a rearmost end of the attachment band 10. The number of hinges 5 and positions thereof may be designed arbitrarily.

Figure 4A:
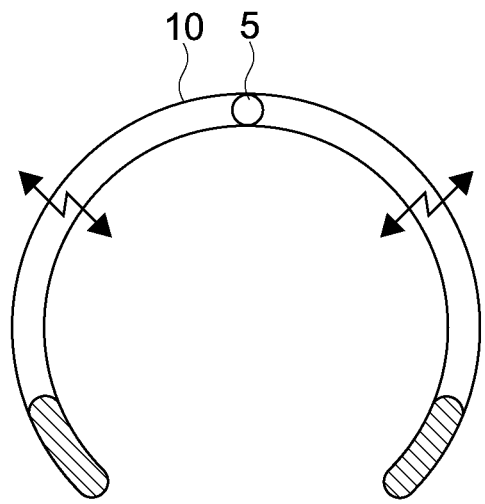
FIGS. 4A, 4B, and 4C Schematic diagrams showing other configuration examples of a driving mechanism.
Figure 4B:
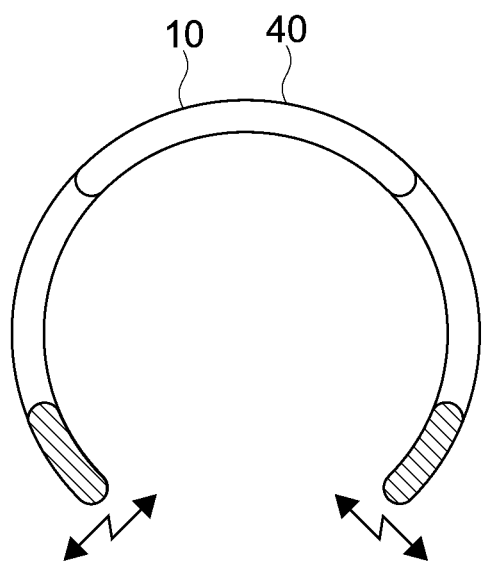

In the driving mechanism shown in FIG. 4B, a multijoint hinge 40 in which a plurality of hinges are arranged on the rear side of the attachment band 10 is provided. Accordingly, it becomes possible to achieve a flexible holding posture with respect to the attachment target. In other words, it becomes possible to increase variations of the holding state.

Figure 4C:
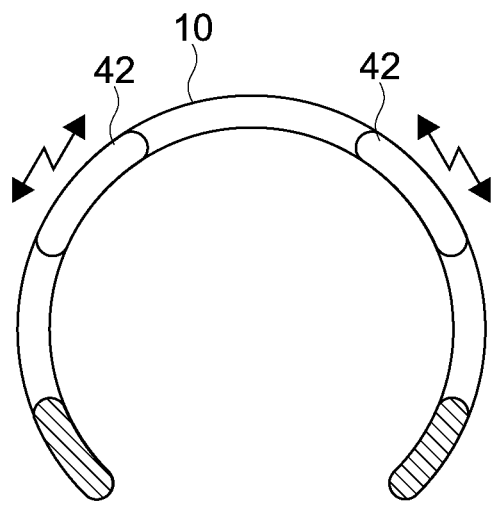

In the driving mechanism shown in FIG. 4C, slide mechanisms 42 are provided at left- and right-hand positions on the rear side of the attachment band 10. When the attachment band 10 is contracted by a sliding operation of the slide mechanisms 42, the holding force is strengthened. When the attachment band 10 is extended, the holding force is weakened.

Figure 5A:
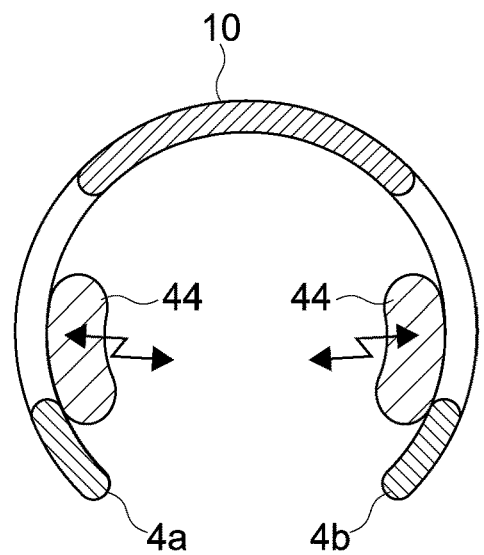
FIGS. 5A, 5B, and 5C Schematic diagrams showing other configuration examples of the driving mechanism.
Figure 5B:
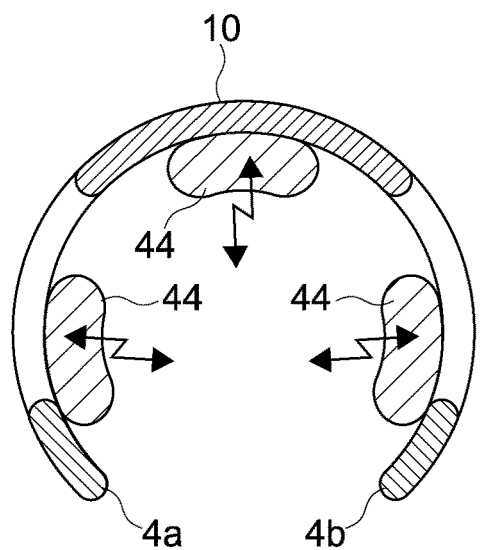

In the driving mechanism shown in FIG. 5A, expansion members 44 that can be inflated by an inflow of air or the like are respectively provided in the vicinity of the left- and right-hand end portions 4a and 4b. In the driving mechanism shown in FIG. 5B, the expansion member 44 is provided on the rear side in addition to the left- and right-hand sides. When the expansion members 44 expand, the holding force is strengthened, and when the expansion members 44 contract, the holding force is weakened. By controlling the expansion amount, it becomes possible to control the holding force. Further, by appropriately selecting the expansion member 44 to be expanded, it becomes possible to control the holding position. Furthermore, by setting the order of expansion and the like, variations of the holding state can be increased. It should be noted that the inflow of air or the like can be executed by a pump or the like.

Figure 5C:
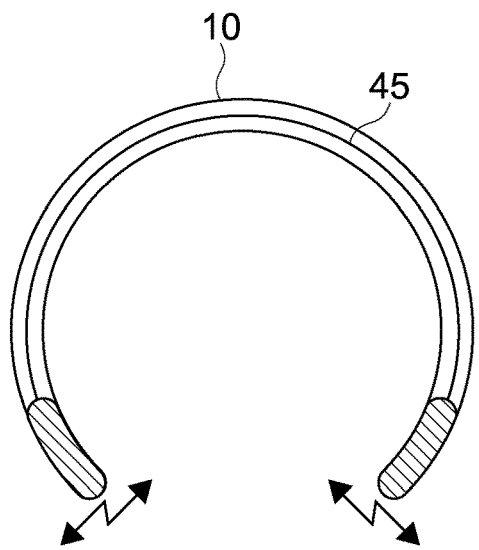

In the driving mechanism shown in FIG. 5C, a shape-memory alloy (SMA) 45 having a characteristic of contracting when electric power is applied is provided inside the attachment band 10. By applying electric power to the SMA 45, the entire attachment band 10 contracts, and the holding force is strengthened. When the application of electric power is stopped, the attachment band 10 returns to its original shape, and the holding force is weakened. By providing a plastic deformation member such as an aluminum plate along the SMA 45, it also becomes possible to maintain a state where the holding force is strengthened without requiring electric power.

Figure 6:
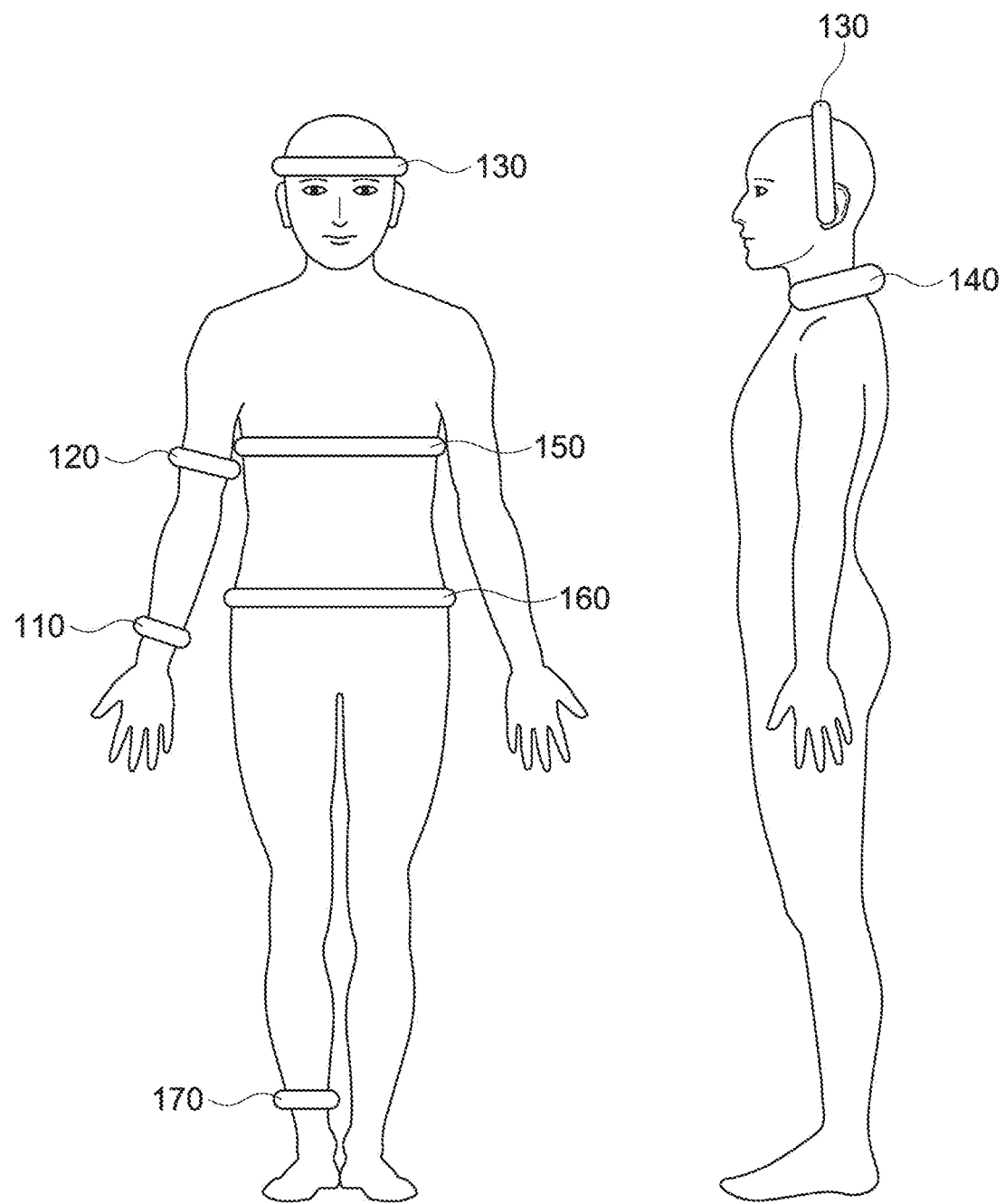
FIG. 6 A diagram for explaining other examples of the wearable apparatus.

FIG. 6 is a diagram for explaining another example of the wearable apparatus 100. As the wearable apparatus 100, there are various forms such as a wristband-type apparatus 110 to be worn at a wrist, a bracelet-type apparatus 120 to be worn at an upper arm, a headband-type (head-mounted type) apparatus 130 to be worn on a head, a neckband-type apparatus 140 to be worn on a neck, an body-type apparatus 150 to be worn at a chest, a belt-type apparatus 160 to be worn at a waist, and an ankle-type apparatus 170 to be worn at an ankle.

Further, ring-type, necklace-type, earring-type, and pierce-type wearable apparatuses and wearable apparatuses usable in shoe soles can also be developed. The present technology is applicable to these various wearable apparatuses. For example, the holding state is determined as appropriate in accordance with an attachment part.

A wearable apparatus that can be used by being worn wherever the user likes among the wrist, the upper arm, the foot set, and the like is also possible. In this case, the controller 18 detects the attachment part as the information of the attachment target. Then, the holding state corresponding to the attachment part is determined as appropriate. For example, the holding state corresponding to the usage state when worn on the wrist, the holding state corresponding to the usage state when worn on the ankle, and the like may be determined to differ from one another. For example, when worn on the ankle, the holding state is determined so that the holding force becomes stronger than that when worn on the wrist.

It should be noted that the present technology is applicable to not only humans but also wearable apparatuses worn on animals and the like. For example, by applying the present technology to a decorative device that becomes a costume for animals or a medical device used for treatment, it becomes possible to suppress a load on animals, and the like.

It should be noted that in a case where the head-mounted-type apparatus 130 is an HMD including a headband that extends in a circumferential direction of the head of the user and is capable of changing its holding force, the holding force of the headband may be changed on the basis of a change in the angular acceleration in the circumferential direction of the head. For example, it is favorable for the holding force of the headband to be strengthened on the basis of the fact that the angular acceleration in the circumferential direction of the head is equal to or larger than a predetermined value. With this configuration, it becomes possible to suppress an occurrence of a deviation of the HMD in a case where the user looks around a virtual space. Alternatively, it is favorable for the holding force of the headband to be weakened on the basis of the fact that the angular acceleration in the circumferential direction of the head is smaller than a predetermined value. With this configuration, since the holding force of the headband can be reduced in a still state of the user where a requisite holding force is smaller than that in the case where the user looks around the virtual space, even in a case where the HMD is used for a long time, the load of the user can be reduced. It should be noted that the value of the angular acceleration in the circumferential direction of the head is included in the operation information that indicates the angular acceleration of the HMD. The holding force of the headband may be changed on the basis of other operation information that indicates the angular acceleration of the HMD.

The driving mechanism for changing the holding force may be, for example, an arbitrary actuator mechanism that uses a motor, a piezoelectric device, a wire, a solenoid, an SMA, or the like. For example, in a case where the headband includes a dial that enables the user to make an arbitrary holding force adjustment, the holding force may be changed by automatically rotating the dial by the motor in accordance with the change in the angular acceleration. Alternatively, the driving mechanism that includes the expansion members that can be inflated by inflow of air or the like in the example described above may be used.

The information related to the usage state and the usage state to be determined can be set arbitrarily. Examples thereof are listed again below.

Information Related to User State

Point of regard (including line of sight, focus, focus position, etc.), behavior recognition result (still, walking, running, climbing up/down stairs, driving automobile), movement speed, biological information (heart rate, body temperature, perspiration, blood pressure, perspiration, pulse, respiration, palpebration, eyeball movement, gaze time, size of pupil diameter, blood pressure, brain waves, body movement, body posture, cutaneous temperature, electric skin resistance, MV (microvibration), myopotential, SPO2 (blood oxygen saturation level)), emotion estimation (delight, anger, sorrow, and pleasure), posture of user, position of user, user setting (manual input), approach to virtual object.

Information Related to Apparatus State of Wearable Apparatus

Device attribute (bracelet, HMD, TV, smartphone), display resolution, display size, display method, HMD method, presence/absence of sensor, ID, remaining battery amount, battery capacity, whether apparatus is being charged or not, CPU processing load, CPU temperature, presence/absence of external storage medium slot, communication method, acoustic characteristics, imager characteristics, 3D shooting, 3D display, device posture, wearable device attachment state (attached, not attached, attached part), device position (if wearable, attachment position).

Background (important information, background color), illuminance, place (indoor, outdoor, situation (geofence), underwater, atmosphere), behavior history (whether user is at familiar place), surroundings (presence/absence of others, cars, etc., density), time, altitude, temperature, direction of wind, air volume.

Information Related to Content

Display size, display position, posture of display, display animation mode (movement speed, movement direction, trajectory, update frequency), content attribute (type, importance degree, priority, type of application (browser, map, mailer, IMF, SNS)), resolution, color, usage mode.

For example, the usage state may be determined on the basis of the various types of information as described above, and the holding state may be controlled as appropriate in accordance with the determined usage state. For example, arbitrary parameters such as a lateral pressure and an expansion amount may be controlled as the holding state.

Devices and functions to be provided in the wearable apparatus are exemplified below.

External input terminal (USB, HDMI), external output terminal (USB, HDMI), Wifi, Bluetooth, external storage medium (memory card) slot, projector, TV, radio tuner, gaze recognition function, audio recognition function, image recognition function (object recognition, character recognition, self-location estimation (SLAM), 3D measurement), gesture recognition function (hand gesture, head gesture), personal authentication function (voiceprint, iris, fingerprint), music/video reproduction function, navigation function, sound image localization function (virtual surround), module for remote control using remote controller.

Interface (wired/wireless) connectable to vehicle (automobile, bicycle, etc.), interface for acquiring information from vehicle (information related to drive) and transmitting information to drive control unit of vehicle.

Interface (wired/wireless) connectable to medical equipment (remote surgery, endoscope), interface for acquiring information from medical equipment (information related to drive) and transmitting information to control unit of medical equipment.

The holding state may be controlled as appropriate on the basis of the information related to the devices and the functions as described above.

An upper limit value of the holding force controllable by the user may be determined. In this case, as the holding state corresponding to the usage state, the holding force is controlled as appropriate within the range equal to or smaller than the upper limit value.

Information on the determined holding state may be referenced when executing other functions. For example, in a case where the photographing mode of the camera is turned ON, the holding state is determined so that the holding force becomes strong. A camera shake correction may be executed by referencing the information on the holding force. For example, control in which the camera shake correction is weakened in a case where the holding force is strengthened, or the like can be executed.

Fine control of the holding states, including a holding state in which the wearable apparatus does not move up and down, a holding state in which the wearable apparatus does not rotate, and the like may be performed. For example, in a helmet-type wearable apparatus or the like, a holding state in which the holding force is strengthened around a horizontal portion at the back of the ear so as to prevent deviations on the left- and right-hand sides, a holding state in which the holding force of a vertical portion extending from the top of the head to the back of the head is strengthened so as to prevent the wearable apparatus from coming off, and the like may be determined as appropriate depending on purposes.

It is also possible to determine a state where the wearable apparatus is not worn and change the holding state accordingly. For example, by changing the holding state to such an extent that an outer shape of the wearable apparatus changes, notification to the user can be performed.

The holding state may be controlled on the basis of only a part of the various types of information described above. For example, the holding state may be controlled as appropriate on the basis of only the information on the user state, only the information on the apparatus state, or only the information on the usage environment.

In the descriptions above, the determination of the holding state and the output of the control information are executed by the controller of the wearable apparatus. Alternatively, an arbitrary computer configured separately from the wearable device may determine the holding state and output the control information.

For example, in a case where a mobile apparatus such as a smartphone and the wearable apparatus are used in an interlocking manner, the determination of the holding state and the output of the control information may be executed by the mobile apparatus. In this case, the mobile apparatus functions as the information processing apparatus according to the present technology. In contrast, it can be said that the wearable apparatus 100 shown in FIGS. 1A and 1B is an apparatus in which the information processing apparatus according to the present technology and the wearable device are integrated. Alternatively, the wearable apparatus 100 itself can also be regarded as the information processing apparatus according to the present technology.

Furthermore, the determination of the holding state and the output of the control information can be executed not only in a computer system constituted of a single computer but also in a computer system in which a plurality of computers operate in an interlocking manner. It should be noted that in the present disclosure, the system means a group of a plurality of constituent elements (apparatuses, modules (components), etc.), and whether all constituent elements are within the same casing is irrelevant. Therefore, a plurality of apparatuses that are accommodated in separate casings and connected via a network and a single apparatus in which a plurality of modules are accommodated in a single casing are both systems.

Execution of the information processing method and program according to the present technology by the computer system includes both the case where the determination of the holding state and the output of the control information are executed by a single computer and the case where respective processing are executed by different computers, for example. Further, the execution of the respective processing by a predetermined computer includes causing another computer to execute a part or all of the processing and acquiring results thereof. For example, the determination of the holding state by a computer A includes outputting information related to the usage state to another computer B, for example, and receiving information on the holding state determined by the computer B.

In other words, the information processing method and program according to the present technology are also applicable to a configuration of cloud computing in which one function is shared and cooperatively processed by a plurality of apparatuses via a network.

At least two of the feature portions according to the present technology described above can be combined. In other words, various feature portions described in the respective embodiments may be arbitrarily combined without distinguishing the embodiments from one another. Moreover, the various effects described above are mere examples and should not be limited thereto, and other effects may also be exerted.

It should be noted that the present technology can also take the following configurations.

(1) An information processing apparatus, including:
  a determination unit that determines, on a basis of information related to a usage state of a wearable device, a holding state of the wearable device with respect to an attachment target; and
  an output unit that generates and outputs control information for achieving the determined holding state.

(2) The information processing apparatus according to (1), in which
  the determination unit determines the usage state of the wearable device and determines the holding state corresponding to the determined usage state.

(3) The information processing apparatus according to (1) or (2), in which
  the holding state includes a holding force and a holding position with respect to the attachment target.

(4) The information processing apparatus according to any one of (1) to (3), in which
  the information related to the usage state includes state information of a user who uses the wearable device.

(5) The information processing apparatus according to (4), in which
  the state information of the user includes motion information, biological information, and positional information.

(6) The information processing apparatus according to (5), in which
  the motion information includes a result of a behavior analysis of the user.

(7) The information processing apparatus according to (5) or (6), in which
  the holding state includes a holding force with respect to the attachment target, and
  the determination unit determines each of a first motion state of the user on a basis of the motion information and a second motion state in which a motion amount is larger than that of the first motion state, and determines, in accordance with the second motion state, a second holding state in which the holding force is larger than that of a first holding state determined in accordance with the first motion state.

(8) The information processing apparatus according to any one of (5) to (7), in which
  the holding state includes a holding force with respect to the attachment target, and
  the determination unit restricts the holding force on a basis of the biological information.

(9) The information processing apparatus according to (8), in which
  the determination unit restricts the holding force in a case where a predetermined user state is determined on a basis of the biological information.

(10) The information processing apparatus according to (9), in which
  the determination unit restricts the holding force by setting an upper limit value of the holding force.

(11) The information processing apparatus according to any one of (1) to (10), in which the information related to the usage state includes state information of the wearable device.

(12) The information processing apparatus according to (11), in which
the state information of the wearable device includes information related to a function of the wearable device.

(13) The information processing apparatus according to (11) or (12), in which
the wearable device is a head-mounted display,
the state information of the wearable device is operation information that indicates an angular acceleration of the head-mounted display, and
the determination unit changes the holding force on a basis of a change of the operation information.

(14) The information processing apparatus according to any one of (1) to (13), in which
the information related to the usage state includes information of a usage environment of the wearable device.

(15) The information processing apparatus according to any one of (1) to (14), in which
the information related to the usage state includes information of the attachment target.

(16) The information processing apparatus according to any one of (1) to (15), in which
the determination unit sets a plurality of candidate holding states as candidates of the holding state, and selects the holding state from the plurality of candidate holding states.

(17) The information processing apparatus according to any one of (1) to (16), in which
the determination unit sets a basic holding state and determines the holding state by changing the basic holding state on a basis of the information related to the usage state of the wearable device.

(18) The information processing apparatus according to any one of (1) to (17), in which
the determination unit is capable of determining a state where a plurality of mutually-different holding states change continuously, as the holding state.

(19) A wearable apparatus, including:
a holding unit that holds an attachment target;
a determination unit that determines a holding state of the holding unit on a basis of information related to a usage state; and
an output unit that outputs control information for achieving the determined holding state to the holding unit.

REFERENCE SIGNS LIST 5, 5a, 5b hinge
8a, 8b holding position
10 attachment band
18 controller
20 sensor unit
21 driving mechanism
23 pressure sensor
24 proximity sensor
25 9-axis sensor
26 GPS
27 biological sensor
29 holding state table
31 determination unit
32 output unit
40 multijoint hinge
42 slide mechanism
44 expansion member
100 wearable apparatus
110 wristband-type apparatus
120 bracelet-type apparatus
130 headband-type (head-mounted type) apparatus
140 neckband-type apparatus
150 apparatus for body
160 belt-type apparatus
170 anklet-type apparatus

The invention claimed is:

1. An information processing apparatus, comprising:
at least one sensor configured to acquire usage information related to a usage state of a wearable device and a current holding state of the wearable device;
an actuator mechanism configured to change the current holding state of the wearable device with respect to a user of the wearable device; and
a processor configured to:
determine, based on the usage information, a holding state of the wearable device, wherein
the current holding state comprises a holding force and a holding position of the wearable device that is configured to exert the holding force; and
control the actuator mechanism to change the holding force based on a determination that the current holding state is different from the determined holding state,
wherein the actuator mechanism is further configured to change the holding force by rotation of a first part of the wearable device with respect a second part of the wearable device.

2. The information processing apparatus according to claim 1, wherein
the at least one sensor is further configured to acquire, as the usage information, at least one of motion information, biological information, or positional information of the user.

3. The information processing apparatus according to claim 2, wherein
the at least one sensor is further configured to acquire the motion information, and
the motion information includes a result of a behavior analysis of the user.

4. The information processing apparatus according to claim 2, wherein
the at least one sensor is further configured to acquire the motion information, and
the processor is further configured to:
determine, based on the motion information, whether the user is in a first motion state or a second motion state, wherein a motion amount of the user in the second motion state is larger than that of the first motion state;
change a current holding force of the actuator mechanism to a first holding force based on the determination that the user is in the first motion state; and
change the current holding force of the actuator mechanism to a second holding force based on the determination that the user is in the second motion state, wherein the second holding force is larger than the first holding force.

5. The information processing apparatus according to claim 2, wherein
the at least one sensor is further configured to acquire the biological information, and
the processor is further configured to:
determine, based on the biological information, whether a physical condition of the user is a bad condition; and decrease a current holding force of the actuator mechanism based on the determination that the physical condition of the user is the bad condition.

6. The information processing apparatus according to claim 1, wherein the at least one sensor is further configured to acquire, as the usage information, state information of the wearable device.

7. The information processing apparatus according to claim 6, wherein
the state information of the wearable device indicates a function that the wearable device is operating, and
the processor is further configured to control, based on a change of the operated function, the actuator mechanism to change the holding force of the actuator mechanism.

8. The information processing apparatus according to claim 6, wherein
the wearable device is a head-mounted display,
the state information of the wearable device is operation information that indicates an angular acceleration of the head-mounted display, and
the processor is further configured to control, based on a change of the operation information, the actuator mechanism to change the holding force of the actuator mechanism.

9. The information processing apparatus according to claim 1, wherein
the at least one sensor is further configured to acquire, as the usage information, information of a usage environment of the wearable device, and
the processor is further configured to control, based on a change of the usage environment, the actuator mechanism to change the holding force of the actuator mechanism.

10. A method, comprising:
acquiring, from at least one sensor, usage information related to a usage state of a wearable device and a current holding state of the wearable device;
determining, by a processor, a holding state of the wearable device based on the usage information, wherein
the current holding state comprises a holding force and a holding position of the wearable device that is configured to exert the holding force; and
controlling an actuator mechanism to change the holding force based on a determination that the current holding state of the wearable device with respect to a user of the wearable device is different from the determined holding state,
wherein the actuator mechanism is configured to change the holding force by rotation of a first part of the wearable device with respect a second part of the wearable device.

11. A non-transitory computer-readable medium having stored thereon computer-executable instructions which, when executed by a processor of an information processing apparatus including at least one sensor, an actuator mechanism, and the processor, cause the processor to execute operations, the operations comprising:
acquiring, from the at least one sensor, usage information related to a usage state of a wearable device and a current holding state of the wearable device;
determining, by the processor, a holding state of the wearable device based on the usage information, wherein
the current holding state comprises a holding force and a holding position of the wearable device that is configured to exert the holding force; and
controlling the actuator mechanism to change the holding force based on a determination that the current holding state of the wearable device with respect to a user of the wearable device is different from the determined holding state,
wherein the actuator mechanism is configured to change the holding force by rotation of a first part of the wearable device with respect a second part of the wearable device.

\* \* \* \* \*